United States Patent
Mathew

[11] Patent Number: 5,132,457
[45] Date of Patent: Jul. 21, 1992

[54] STEREOSPECIFIC SYNTHESIS OF 2(R)-2-METHYL-3-DIMETHYLAMINO-PROPIOPHENONE (D-DAMP)

[75] Inventor: Jacob Mathew, Fenton, Mo.

[73] Assignee: Mallinckrodt Specialty Chemicals Company, St. Louis, Mo.

[21] Appl. No.: 749,855

[22] Filed: Aug. 26, 1991

[51] Int. Cl.$^5$ .................. C07C 209/46; C07C 209/68
[52] U.S. Cl. .................................... 564/343; 564/342
[58] Field of Search ............................... 564/343, 342

[56] References Cited

U.S. PATENT DOCUMENTS 4,980,377 12/1990 Lafon ........................ 544/342 X

OTHER PUBLICATIONS

Brown and Devant, *Tetrahedron Letters*, 25:5031–5034 (1984).
Evans et al., *J. Am. Chem. Soc.* pp. 106, 1154–1156 (1984).
Evans et al., *J. Am. Chem. Soc.* 103:2999–3111 (1981).
Gage, J. R. and Evans D. A., *Organic Synthesis*, vol. 68 pp. 77, 83 (1989).
Erickson, T. J., "Asymmetric Synthesis of Darvon Alcohol," *J. Org. Chem.*, vol. 51, pp. 934–935 (1986).
Pohland, A. and Sullivan, H. R., *J. Am. Chem. Soc.*, vol. 77, p. 3400.
Evans, D. A. et al., Stereoselective Aldol Condensations via Boron Enolates, *J. Am. Chem. Soc.*, vol. 103, pp. 3099–3111 (1981).
Parikh, J. R. and Doering, W., *J. Am. Chem. Soc.*, vol. 89, pp. 5505–5507 (1967).
Pohland, et al., *J. Org. Chem.*, vol. 28, p. 2483 (1963).

*Primary Examiner*—Richard L. Raymond
*Attorney, Agent, or Firm*—Rothwell, Figg, Ernst & Kurz

[57] ABSTRACT

In a method for producing 2(R)-2-methyl-3-dimethylamino-propiophenone (d-DAMP), a chiral ester of the formula

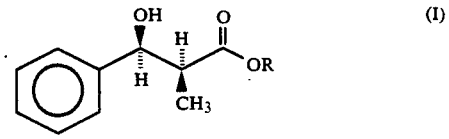

(I)

wherein R is an alkyl of from 1 to about 5 carbon atoms, is provided. The chiral easter of formula (I) is converted into a chiral amino-alcohol of the formula

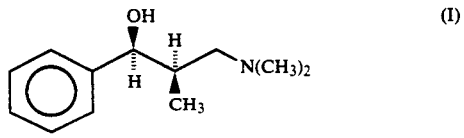

(I)

and the chiral amino-alcohol is oxidized so as to form d-DAMP.

19 Claims, No Drawings

STEREOSPECIFIC SYNTHESIS OF 2(R)-2-METHYL-3-DIMETHYLAMINO-PROPIOPHENONE (D-DAMP)

FIELD OF THE INVENTION

The present invention relates generally to obtaining stereospecific d-DAMP.

BACKGROUND OF THE INVENTION

The compound 2(R)-2-methyl-3-dimethylaminopropiophenone (d-DAMP) is useful as an intermediate in the stereospecific synthesis of α-d-4-dimethylamino-1,2-diphenyl-3-methyl-2-butanol (d-oxyphene) which, in turn, is an intermediate in the synthesis of d-propoxyphene, the propionyl ester of d-oxyphene.

Previously, intermediate d-oxyphene has been produced by resolving d-DAMP through crystallization of stereospecific tartate salts and then by reacting the d-DAMP with benzylmagnesium chloride. Pohland, et al., *J. Org. Chem.*, Vol. 28, p 2483 (1963). Alternatively, intermediate d-oxyphene has been produced using a tetrasubstituted epoxy alcohol intermediate. Erickson, T., "Asymetric Synthesis of Darvon Alcohol," *J. Org. Chem.*, Vol. 51, p. 934–935 (1986). These procedures, by which intermediate d-oxyphene has previously been synthesized, are lengthy, inefficient and expensive ways to produce the end product d-propoxyphene.

The end product d-propoxyphene is recognized and accepted as possessing effective analgesic qualities in humans, whereas, 1-propoxyphene does not possess these same qualities. Pohland, A., and Sullivan, H.R, "Preparation of α-d- and α-1-4-Dimethylamino-1,2-diphenyl-3-methyl-2-propionyloxy butane," *J. Am. Chem. Soc.*, Vol. 77, p 3400 (1955).

When producing a stereospecific compound such as d-propoxyphene, it would be highly desirable to start with a substantially pure stereospecific precursor such as d-DAMP.

To date, there has not been a quick, efficient process for synthesizing substantially pure stereospecific d-DAMP. Previous methods in which stereospecific end products, such as d-propoxyphene, have been synthesized through stereospecific intermediates, such as d-DAMP, are lengthy procedures (e.g., reacting d-DAMP with a stereospecific tartate and benzylmagnesium chloride) in which the end product is produced inefficiently and in poor yields. A method is, therefore, needed which can synthesize stereospecific d-DAMP, quickly, efficiently, and in high yields so that this compound can be used as a precursor in the organic synthesis of d-propoxyphene.

SUMMARY OF THE INVENTION

In accordance with the present invention, a method for producing d-DAMP comprises providing a chiral ester of the formula (I)

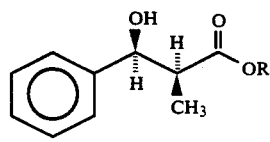

wherein R is an alkyl of from 1 to about 5 carbon atoms; converting said chiral ester into a chiral amino-alcohol of the formula (II)

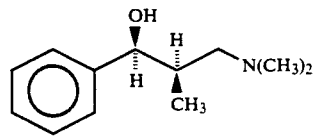

and oxidizing the chiral amino-alcohol of formula (II) so as to form d-DAMP.

DETAILED DESCRIPTION OF THE INVENTION

The process of the present invention utilizes a chiral ester of the formula (I) as set forth above, wherein R is an alkyl of from 1 to about 5 carbon atoms, preferably an alkyl from 1 to about 3 carbon atoms, more preferably, an alkyl of from about 1 to about 2 carbon atoms, and most preferably, methyl.

In preferred embodiments, the chiral ester of the formula (I) is provided by converting a corresponding chiral acid into the chiral ester of formula (I). The corresponding chiral acid, from which the chiral ester of formula (I) is produced, can be synthesized as disclosed in Gage, et al., *Organic Synthesis*, 68:83 (1989).

The chiral acid can be converted into the chiral ester of formula (I) in the presence of an alkyl halide of the formula R-X, wherein R is as defined above and X is halogen. In preferred embodiments, the alkyl halide is methyl iodide, and the reaction occurs in the presence of $NaHCO_3$ and dimethylformamide (DMF) so as to obtain the chiral ester of formula (I).

According to the present invention, the chiral ester of formula (I) is converted into a chiral amino-alcohol of the formula (II) as set forth above. During conversion of the chiral ester of formula (I) into the chiral amino-alcohol of formula (II), the chiral ester of formula (I) is reduced so as to provide its corresponding chiral diol. This can be accomplished by reacting the chiral ester with a suitable reducing agent, such as lithium aluminum hydride ($LiAlH_4$), in a non-polar solvent such as tetrahydrofuran (THF).

In preferred embodiments, the chiral diol thus produced is transformed into a corresponding chiral monotosylate. The chiral diol is transformed into the chiral monotosylate in the presence of a tosyl halide, such as tosyl chloride (TsCl). This reaction can take place with sodium hydroxide (NaOH) in a non-polar solvent such as tetrahydrofuran, so as to obtain the chiral monotosylate.

In accordance with one aspect of the invention, the chiral monotosylate thus produced is transformed into a corresponding chiral amino-alcohol of formula (II) set forth above. The chiral monotosylate can be transformed into the corresponding chiral amino-alcohol of formula (II) by reacting the chiral monotosylate with dimethylamine. The reaction can take place in a polar aprotic solvent such as dimethylsulfoxide (DMSO), dimethylformamide (DMF), acetonitrile, and the like, so as to obtain the corresponding amino-alcohol of formula (II). In a preferred embodiment, the polar aprotic solvent is DMSO. This reaction can be carried out over a period of about two days at a temperature of about 25° C.

As noted above, the chiral amino-alcohol of formula (II) is oxidized so as to form d-DAMP. Oxidation is accomplished by reacting the chiral amino-alcohol with an oxidizing agent, such as sulfurtrioxide pyridine ($SO_3$·

Pyr). In particularly preferred embodiments, the oxidation reaction takes place in a DMSO/triethylamine (Et₃N) solution.

The invention is further illustrated by the following examples, which are not intended to be limiting.

EXAMPLE I (2)-4-(phenylmethyl)-2-oxazolidinone was produced in accordance with the teachings of Gage et al., *Organic Synthesis*, 68:77 (1989). The (S)-4-(phenylmethyl)-2-oxazolidinone thus obtained was reacted with benzaldehyde in the presence of tributylborontriflate and triethyl amine. The resulting aldol adduct was isolated in 86% yield and was shown by NMR shift studies to be at least 87% chirally pure. In the next step the aldol was hydrolysed with LiOH and 30% hydrogen peroxide to give, after simple extraction technique, a chiral acid and (S)-4-(phenylmethyl)-2-oxazolidinone. The chiral oxazolidinone was recovered almost quantitatively and can be recycled. The chiral acid was converted to a chiral ester using NaHCO₃ and methyl iodide in DMF. The chiral ester on analysis by proton NMR was shown to be at least 96.5% chirally pure. Reduction of this ester with LiAlH₄ in THF gave the chiral diol, according to the Scheme shown below. The chiral diol then was converted to the monotosylate using NaOH/TsCl in THF. The crude tosylate was stirred with excess dimethylamine in DMSO for 2 days to give a chiral monoalcohol. Oxidation of this chiral mono-alcohol with SO₃·Pyr in DMSO/triethylamine gave the target chiral compound d-DAMP in 35% overall yield. The d-DAMP was shown to be at least about 96.5% chirally pure by chiral High Performance Liquid Chromatography and by NMR analysis. The reaction scheme is shown below.

SCHEME

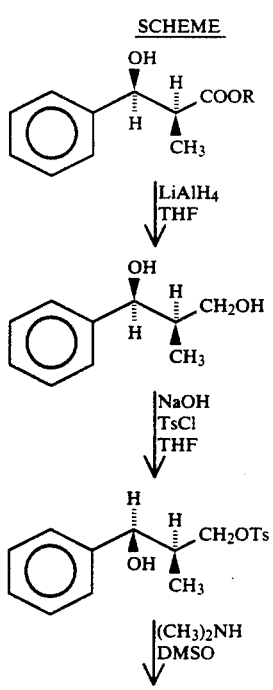

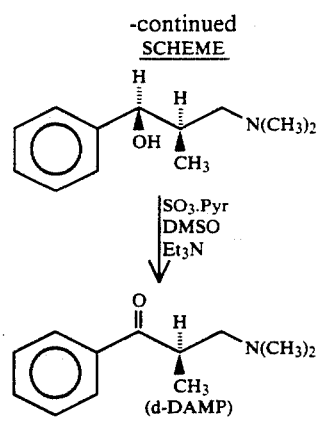

(d-DAMP)

EXAMPLE II

To (S)-4-(Phenylmethyl)-2-oxazolidinone (17.5 g, 0.1 mole) in THF (250 ml) at −70° C. under a blanket of nitrogen was added 2.5M n-BuLi (0.11 mole, 44 ml) dropwise in 10 minutes. After 5 minutes, the clear cloudy solution was treated rapidly with propionyl chloride (10 g, 0.105 mole). The colorless solution was then slowly warmed to room temperature in the course of 1 hour, quenched with saturated ammonium chloride (20 ml) and diluted with ether (100 ml). The organic extract washed with water (20 ml), aqueous NaHCO₃ (20 ml), dried over anhydrous MgSO₄ and evaporated to give a viscous solid mass. Trituration with hexane (100 ml) gave the oxazolidinone 3-(1-OxoPropyl)-(S)-4-(Phenylmethyl)-2-Oxazolidinone (21 g, 90%) as white plates MP.44°–46° C.IR:3030, 2980, 1780, 1705, 1455 cm⁻¹.

EXAMPLE III

To a solution of 3-(1-OxoPropyl)-(S)-4-(Phenylmethyl)-2-Oxazolidinone (12 gms, 50 m.mole) in methylene chloride (100 ml) at −10° C. under nitrogen was added a 1M solution of dibutyl boron triflate (55 ml, 55 m.mole) in methylene chloride. After 10 minutes, the deep orange solution was treated dropwise with triethyl amine (6 g, 60 m.mole). To this pale yellow solution was added via syringe a solution of benzaldehyde (5.4 g, 52 m.mole) in methylene chloride (10 ml). The orange solution stirred at −10° C. for 90 minutes and then quenched with a solution of methanol (100 ml) and p^H 7 aqueous phosphate buffer (50 ml). To this cloudy solution was added a solution of 1:2 30% Hydrogen peroxide in methanol (150 ml) dropwise in 20 minutes keeping the internal temperature below 10° C. The clear solution stirred at room temperature for 1 hour and then the solvents were evaporated under vaccuu at 35° C. The residue was diluted with ether (200 ml) and washed with water (20 ml). The combined aqueous layer extracted with ether (3×60 ml) and the organic layers combined, washed with aqueous NaHCO₃ (2×20 ml), brine (10 ml), dried over anhydrous MgSO₄ and evaporated to give yellow powder. This was triturated with hot hexane to give the desired aldol A (below) (16 g, 94%) as pale yellow powder. MP.92° C. H NMR:δ1.20(d,3H), 2.80(dd,1H), 3.10(d,1H, J=2.7), 3.30(dd,1H,J=13.4), 4.1 (m,3H), 4.60 (m,1H), 5.1(m,1H), 7.1–7.5(m,10H).

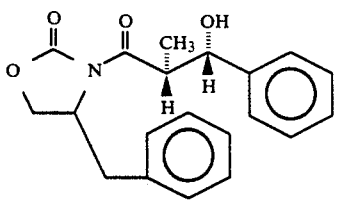

(A)

EXAMPLE IV

To a stirred solution of A (above) (6.8 g, 20 m.mole) in 4:1 THF:water (125 ml) at 0° C. under nitrogen was added 30% hydrogen peroxide (10 ml) and then after 5 minutes a solution of LioH.H$_2$O (1.7 g, 30 m.mole) in water (50 ml) was added via syringe. The clear solution stirred for 1 hour at 0° C. and then quenched with a saturated solution of sodium bisulfite (70 ml). After 30 minutes at room temperature the solvents (THF) were removed under vaccu and the residue diluted with water (20 mL) and extracted with methylene chloride (3×100 ml). The aqueous layer was separated and acidified with 2NHCl till pH was attained. The resulting oil was extracted with ether (3×60 ml) and the organic extract washed with water (10 ml) and dried over MgSO$_4$. Evaporation of solvents and trituration with 1:1 hexane-CCl$_4$ (10ml) gave the chiral acid (2S,3S)-2-Methyl-3-phenyl-3-hydroxy-propanoic acid (3.3 g, 91%) as white plates Mp.89°-90° C. $^1$H NMR: δ1.20(d,3H), 2.9(m,1H), 5.20(d,1H), 7.20-7.40(m,5H). IR: 3600, 3040, 3000, 1710, 1455 cm$^{-1}$.

EXAMPLE V

To a stirred solution of acid (2S,3S)-2-Methyl-3-phenyl-3-hydroxy-propanoic acid (3.3 g, 18.3 m.mole) in DMF (15 ml) under nitrogen was added powdered NaHCO$_3$ (2.6 g, 30 mmole) and methyl iodide (7 g, 50 m.mole). The yellow solution was stirred at room temperature for 14 hours. The thick cake was then poured into ice water (50 ml) and extracted with ether (2×40 ml). The organic extract washed with water (10 ml), saturated sodium thiosulfate (2×20 ml), brine (10 ml) and dried over MgSO$_4$. Evaporation gave viscous oil. Flash column chromatography on silica gel and eluting with 5% EtOAc/hexane gave the pure chiral ester (2S,3S)-Methyl -2-methyl-3-phenyl-3-hydroxy-propionate (3.1 g, 87%) as a colorless viscous oil. $^1$H NMR: δ1.20(d,3H), 2.90(m,1H), 3.70(s,3H), 5.20(d,1H), 7.2-7.40(m.5H). Chiral shift study using tris[3-(heptafluoropropylhydroxymethylene-(+)camphorato], europium(III) showed the enantiomer ratio to be 96.8:3.2.

EXAMPLE VI

To a stirred solution of the chiral ester (2S,3S)-Methyl-2-methyl-3-phenyl-3-hydroxy-propionate (3.1 g, 16 m.mole) in THF (10 ml) at ice bath temperature under nitrogen was added dropwise a 1M solution of LAH in ether (34 ml, 34 m.mole) via syringe. The cloudy suspension stirred at room temperature for 12 hours and then quenched with ice water (2 ml), 2N NaOH (3 ml) and water (2 ml). The thick cake was diluted with ether (100 ml), filtered over celite and the filtrate washed with water (20 ml) and dried over anhydrous MgSO$_4$. Evaporation of solvents gave crude diol (2S,3S)-2-Methyl-3-phenyl-3-hydroxy-1-propanol (2.5 g, 94%) as a viscous oil sufficiently pure for the next step. $^1$H NMR δ0.85(d,3H), 2.05(m,1H), 3.78(d,2H), 4.85(d,1H), 7.20(m,5H). Chiral shift study established the enantiomer ratio to be 97:3.

EXAMPLE VII

To a stirred solution of diol (2S,3S)-2-Methyl-3-phenyl-3-hydroxy-propanol (2.5 g,15 m.mole) in THF (20 ml) was added NaOH (1 g, 40 m.mole) and Tosyl chloride (5 g, 25 m.mole) in THF (5 ml). The cloudy solution was stirred at room temperature for 6 hours and then THF was evaporated under vaccu, diluted with ether (50 ml) washed with water (2×10 ml) and dried over anhydrous MgSO$_4$. Evaporation gave crude tosylate (2S,3S)-2-Methyl-3-phenyl-3-hydroxy-1-tosyloxy-propane (4.1 g, 85%) sufficiently pure for the next step as a yellow viscous oil.

EXAMPLE VIII

To a stirred solution of the tosylate (2S,3S)-2-Methyl-3-phenyl-3-hydroxy-1-tosyloxy-propane (4.1 g, 12.8 m.mole) in DMSO (15 ml) was added 40% aqueous dieethylamine (20 ml, excess) and kept in a sealed vessel for 2 days. The mixture then poured into ice water (40 ml) and extracted with ether (2×30 ml). The organic extracts washed with water (3×10 ml) and then extracted with 1N HCl (3×15 ml). The aqueous acidic extract treated with aqueous ammonium hydroxide until basic and then extracted with ether (2×30 ml). The ether extract washed with water (2×10 ml), dried over MgSO$_4$ and evaporated to give amine (1S,2S)-3-dimethylamino-2-methyl-1-phenyl-1-propanol (1.6 g, 70%) as a yellow powder. Mp. 61°. $^1$H NMR: δ0.80 (d,3H), 1.90 (1H,m), 2.10 (2H,m), 2.40 (s,6H), 4.75 (m,1H), 7.25 (s,5H). Chiral shift study established that the enantiomer ratio was 97:3 with no trace of epimerisation.

EXAMPLE IX

To a stirred solution of (1S,2S)-3-dimethylamino -2-methyl-1-phenyl-1-propanol (1.86 g, 10 m.mole) in DMSO (14 ml) at ice bath temperature was added tirethyl amine (4.4 g, 44 m.mole) and then sulfur trioxide.-pyridine (4.7 g, 30 m.mole). The mixture was then warmed to room temperature and stirred at room temperature for 2 hours. The brown solution was poured into ice-water (30 ml) and extracted with ether (2×20 ml). The organic extract washed with brine (3×10 ml), dired over anhydrous magnesium sulfate and solvents evaporated under vaccu to give crude 2-(R)-3-dimethylamino-2-methyl-propiophenone (d-DAMP) (1.2 g, 64%) as a pale yellow oil. $^1$H NMR: δ1.55(d,3H), 2.85(m,2H), 3.10(s.6H), 3.85(m, 1H), 7.60(M,3H), 8.40(m,2H). Chiral shift study showed it be at least 97% d-DAMP. Chiral HPLC supported this result.

What is claimed is:

1. A method for producing d-DAMP, comprising providing a chiral ester of the formula

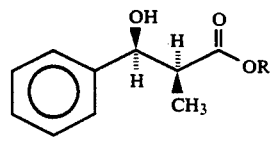

(I)

wherein R is an alkyl of from 1 to about 5 carbon atoms; converting said chiral ester into a chiral amino-alcohol of the formula

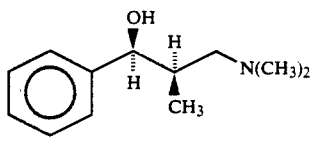 (I)

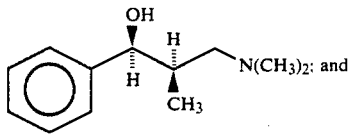 (II)

and oxidizing said chiral amino-alcohol so as to form d-DAMP.

2. The method of claim 1 wherein said chiral ester is provided by converting a corresponding chiral acid into said chiral ester.

3. The method of claim 2 wherein said chiral acid is converted into said chiral ester in the presence of an alkylhalide of the formula R-X, wherein R is as defined, and X is halogen.

4. The method of claim 3 wherein said alkylhalide is methyl iodide.

5. The method of claim 1 wherein the converting step includes the step of reducing said chiral ester so as to provide a corresponding chiral diol.

6. The method of claim 5 wherein said chiral ester is reduced to said chiral diol in the presence of LiAlH$_4$.

7. The method of claim 5 wherein the converting step includes the step of transforming the chiral diol into a corresponding chiral monotosylate.

8. The method of claim 7 wherein said chiral diol is transformed into said chiral monotosylate in the presence of a tosyl halide.

9. The method of claim 8 wherein said tosyl halide is tosyl chloride.

10. The method of claim 7 wherein the converting step includes the step of transforming said chiral monotosylate into said chiral amino-alcohol.

11. The method of claim 10 wherein the chiral monotosylate is transformed into the chiral amino-alcohol in the presence of dimethylamine.

12. A method for producing d-DAMP, comprising:
a) providing a chiral ester of the formula

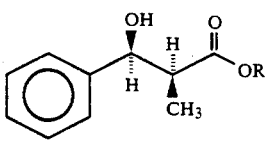 (I)

wherein R is an alkyl of from 1 to 5 carbon atoms;
b) reducing said chiral ester so as to provide a corresponding chiral diol;
c) reacting said chiral diol in the presence of a tosyl halide so as to form a corresponding chiral monotosylate;
d) reacting said chiral monotosylate in the presence of dimethylamine so as to form a chiral amino-alcohol of the formula e) oxidizing said chiral amino-alcohol so as to form d-DAMP.

13. The method of claim 12 wherein said chiral ester is provided by converting a corresponding chiral acid into said chiral ester.

14. The method of claim 13 wherein said chiral acid is converted into said chiral ester in the presence of an alkylhalide of the formula R-X, wherein R is as defined, and X is halogen.

15. The method of claim 14 wherein said alkylhalide is methyl iodide.

16. A method for producing d-DAMP, comprising:
a) providing a chiral ester of the formula

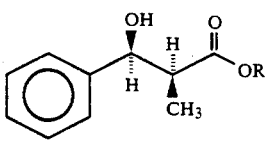 (I)

wherein R s an alkyl of from 1 to about 5 carbon atoms;
b) reducing said chiral ester in the presence of LiAlH$_4$ so as to provide a corresponding chiral diol;
c) reacting said chiral diol in the presence of a tosyl chloride so as to form a corresponding chiral monotosylate;
d) reacting said chiral monotosylate in the presence of dimethylamine so as to form a chiral amino-alcohol of the formula

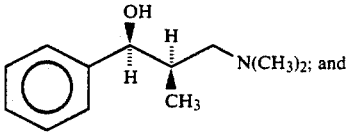 (II)

e) oxidizing said chiral amino-alcohol so as to form d-DAMP.

17. The method of claim 16 wherein said chiral ester is provided by converting a corresponding chiral acid into said chiral ester.

18. The method of claim 17 wherein said chiral acid is converted into said chiral ester in the presence of an alkylhalide of the formula R-X, wherein R is as defined, and X is halogen.

19. The method of claim 18 wherein said alkylhalide is methyl iodide.

* * * * *

UNITED STATES PATENT AND TRADEMARK OFFICE
CERTIFICATE OF CORRECTION

PATENT NO. : 5,132,457
DATED      : July 21, 1992
INVENTOR(S) : Mathew

It is certified that error appears in the above-identified patent and that said Letters Patent is hereby corrected as shown below:

In the Abstract, second paragraph, line 2, delete "easter" and insert --ester--.

Col. 4, line 65, delete "H", and insert --$^1$H--.

Col. 5, line 48, delete "61.20(d,3H), and insert --$\delta$1.20(d,3H)--.

Col. 8, claim 16, line 29, after "R", delete "s" and insert --is--.

Signed and Sealed this

Seventh Day of December, 1993

Attest:

BRUCE LEHMAN

Attesting Officer

Commissioner of Patents and Trademarks